United States Patent [19]

Iscowitz

[11] 3,977,826

[45] Aug. 31, 1976

[54] TERPENOID STABILIZERS IN AEROSOL CO-DISPENSING HAIR COLORING SYSTEMS

[75] Inventor: Sigmund Iscowitz, Flushing, N.Y.

[73] Assignee: Clairol Incorporated, New York, N.Y.

[22] Filed: Feb. 21, 1975

[21] Appl. No.: 551,944

Related U.S. Application Data

[62] Division of Ser. No. 448,130, March 4, 1974, abandoned.

[52] U.S. Cl. ........................................ 8/10.2; 8/11; 8/32; 8/111; 252/186; 424/DIG. 1; 424/DIG. 3; 424/47; 424/62
[51] Int. Cl.² .......................................... A61K 7/13
[58] Field of Search ..................... 424/62, 130, 338; 8/10.2, 11, 32, 111; 423/584; 252/186

[56] References Cited
UNITED STATES PATENTS

| | | | |
|---|---|---|---|
| 274,789 | 3/1883 | Kingzett et al. | 424/130 |
| 2,022,860 | 12/1935 | Kunz | 424/130 |
| 3,339,802 | 9/1967 | Weiner et al. | 8/10.2 |
| 3,488,138 | 1/1970 | Iscowitz | 8/10.2 X |
| 3,499,844 | 3/1970 | Kibbel et al. | 252/316 |
| 3,651,931 | 3/1972 | Hsuing | 8/10.2 X |

FOREIGN PATENTS OR APPLICATIONS

| | | | |
|---|---|---|---|
| 91,285 | 3/1897 | Germany | 424/130 |

*Primary Examiner*—Albert T. Meyers
*Assistant Examiner*—Vera C. Clarke
*Attorney, Agent, or Firm*—David J. Mugford; George A. Mentis; Samuel J. DuBoff

[57] ABSTRACT

Terpenes and their derivatives provide improved stability to aqueous solutions containing hydrogen peroxide as well as to aerosol co-dispensing hair coloring systems containing oxidation dye compositions.

4 Claims, No Drawings

TERPENOID STABILIZERS IN AEROSOL CO-DISPENSING HAIR COLORING SYSTEMS

This is a division of application Ser. No. 448,130, filed 3/4/74, now abandoned.

BACKGROUND OF THE INVENTION

In the dyeing of human hair with direct dyes as distinguished from oxidation dyes, the resultant final color is a combination of the natural hair color plus the color added by the dye. Other procedures utilizing oxidation dyes first eliminate the natural pigments of the hair through bleaching with an oxidizing agent such as alkaline hydrogen peroxide. Then the desired coloration is obtained on the hair by treating the hair with oxidation dyestuffs. Colored polymeric compounds of high molecular weight are produced on the hair by the action of atmospheric oxygen or by oxidizing agents such as hydrogen peroxide. Possible also is the carrying out of simultaneous bleaching and coloring. Concurrently hair is bleached by alkaline hydrogen peroxide as dyestuff penetrates into the hair and is oxidized to produce the desired color.

Usually, the whole operation of bleaching and coloring is accomplished by applying a mixture of oxidizing hair coloring and hydrogen peroxide prepared immediately before application. However, this method takes some time and is subject to errors of mixing yielding insufficient coloring or hair damage by use of excess peroxide. Where there is a delay for one reason or another in applying the mixture to the hair, undesirable coloring effects may result if a partially oxidized mixture is used.

The packaging of oxidizing compositions for hair coloring in containers for distribution under pressure can avoid certain of the disadvantages enumerated. Such a container has two separate interior compartments for maintaining separately the oxidation dye and peroxide portions under pressure. Necessarily, the contents are kept separate until actual use. The mixed composition remains useful only for a short time after it is mixed. Examples of such containers are given in U.S. Pat. Nos. 3,272,389; 3,341,418; and 2,973,883.

The oxidation dye solution lies in the body of the container with the hydrogen peroxide stored in a collapsable bag usually made of plastic material attached to the valve body and partially suspended in the oxidation dye solution. Mixing of the oxidation dye solution and the hydrogen peroxide occurs in the valve housing on actuation of the valve. The mixture coming from the nozzle of the can is directly applied onto the hair. There the mixture is worked into the hair and coloring of the hair occurs.

Dilute solutions (10–20%) of hydrogen peroxide are generally used in this type of package. The most stable of these commercial solutions of hydrogen peroxide slowly liberates oxygen. The liberated oxygen permeates the bag and gradually oxidizes the oxidation dye solution. As a result of this, an undesirable coloring effect will take place when the partially oxidized oxidation dye solution is used. Also, the bag containing the hydrogen peroxide is permeable to vapors from the oxidation dye solution which will lower the hydrogen peroxide stability, resulting in the generation of more oxygen.

Although the best guarantee for high stability of hydrogen peroxide is high purity, some substances prevent or slow down the decomposition for long periods of time. The anticatalytic or stabilizing action of these substances is due to their ability to remove positive catalysts. One group accomplishes this by forming complexes with heavy-metal ions, the other by absorbing these ions and thereby inactivating them. To the first group belong substances such as pyrophosphates, fluorides, cyanides, and some organic substances such as acetanilide, phenacetin, 8-hydroxy quinoline, hydroxy acridines and other chelating agents, examples of which are disclosed in U.S. Pats. Nos. 3,378,444 and 3,632,295; to the second group belong freshly precipitated alumina and silica, sodium stannate, and hydrous antimony and stannic oxides.

However, even in the presence of the most effectively known of these peroxide stabilizers, some peroxide decomposition occurs and oxygen is liberated. The terpenoid stabilizers of the present disclosure will react with this free oxygen, minimizing pressure buildup and permitting for less oxygen to permeate into the dye phase.

Generally, substances which react with oxygen are not stable in the presence of hydrogen peroxide; surprisingly the terpenoids disclosed herein appear to be.

To avoid gas interchange, aluminum-laminated bags can be used. This dose eliminate, to a great extent, vapor permeation into the bag and oxygen permeation out of the bag. However, oxygen is still being slowly liberated from the dilute hydrogen peroxide (10–20%). With more or less no means of escaping, the oxygen in building up swells the bag. This can cause bag rupture. Belgian Pat. No. 746,286 provides for an inner compartment wall that is easily rupturable relative to the outer container wall when a slight increase in pressure results due to liberation of oxygen by the hydrogen peroxide, allowing the liberated oxygen to react with one of the color modifiers (e.g. β-naphthol) to prevent rupture of the container wall by explosion. However, this may render the oxidation dye mixture quickly unsuitable for use, as well as accelerate the breakdown of the hydrogen peroxide liberating more gaseous oxygen. The formation of gaseous oxygen leads to the elevated pressures in the container leading to the danger of explosion unless special precautions are taken in the construction of the container.

The present invention provides for the pickup of oxygen from slowly decomposing dilute hydrogen peroxide before it can escape into the portion of the container carrying the oxidation dye solution. Monoterpenoid compounds, and in particular d-limonene, can be used as the oxygen scavenger. As the monoterpenoids are immune to the action of hydrogen peroxide, they can be placed right at the source of the liberated oxygen.

With only minimal amounts of oxygen now able to escape into the oxidation dye solution, greater efficacy for the antioxidants present in the oxidation dye solution can be expected. Stability of the oxidation dye solution is greatly enhanced. In the aluminum-laminated bag, removal of the slowly liberated oxygen can assure negligible bag expansion so preventing finally bag bursting. The separation barrier between oxidation dye solution and hydrogen peroxide is maintained in the package. Rapid hydrogen peroxide decomposition by interaction with the oxidation dye solution resulting in the formation of gaseous oxygen and dangerously elevated pressure is prevented.

SUMMARY OF THE INVENTION

A stabilized aqueous hydrogen peroxide solution comprising from about 10 to 20 weight percent of hydrogen peroxide, from about 0.25 to 1.4 weight percent of at least one monoterpenoid compound wherein the chemical structure of said compound is acyclic, monocyclic or bicyclic, and the remaining portion of the solution consisting essentially of water is disclosed.

Also disclosed is a hair treatment composition suitable for release from an aerosol container under pressure wherein prior to release the composition is physically separated into mixtures A and B, wherein:

a. mixture A comprises a stabilized aqueous hydrogen peroxide solution comprising from about 10 to 20 weight percent of hydrogen peroxide, from about 0.25 to 1.4 weight percent of at least one monoterpenoid compound wherein the chemical structure of said compound is acyclic, monocyclic or bicyclic, and the remaining portion of the solution consisting essentially of water; and b. mixture B is an aerosol hair dye composition comprising a propellant blend and an aqueous oxidation hair dye concentrate, said concentrate containing at least one oxidation dye intermediate whose color is developable by means of an oxidizing agent.

Usually in the hair treatment composition, the concentrate comprises about 90 to 97 weight percent and the propellant comprises about 3 to 10 weight percent in mixture B. Also, the preferred monoterpenoid compound is d-limonene.

DETAILED DESCRIPTION OF THE INVENTION

The terpenoid compounds of interest herein are described in detail in the "Encyclopedia of Chemical Technology" edited by R. E. Kirk and D. F. Othmer published by The Interscience Encyclopedia, Inc. of New York (1954), in Volume 13 at pages 705 to 771. Generally, terpenes are acyclic and cyclic hydrocarbons whose molecular formulas are some multiple of $C_5H_8$ (i.e. isoprene). Usually, the definition is expanded to include alcohols, aldehydes, ketones and other derivatives thereof which have the same carbon skeleton as the parent terpene hydrocarbon. The terpenes and such additional derivatives are more properly referred to as "terpenoids" which will be used hereinafter to include terpenes.

Most of the terpenoid family of hydrocarbons have carbon skeletons which can be considered condensation products of isoprene. Therefore, such substances can be classified according to the number of isoprene units contained therein such as hemiterpenoids — $C_5H_8$, monoterpenoids — $C_{10}H_{16}$, sesquiterpenoids — $C_{15}H_{24}$, etc. Furthermore, these classes of terpenoids may be further subdivided into acyclic, monocyclic, bicyclic, etc. depending on the number of ring systems formed within the compound.

Although it is felt that the vast majority of the many terpenoid compounds would provide stability to the hydrogen peroxide and coloring compositions to be disclosed herein, due to the ready availability of the monoterpenoids these appear to be the only practical compositions for use herein and are therefore preferred.

Examples of useful acyclic monoterpenes are alloocimene, myrcene and geraniolene. Further examples of acyclic alcohols are citronellol, geraniol, nerol, rhodinol and linalool; additionally, an example of an acyclic aldehyde is citral. Typical examples of useful monocyclic monoterpenoids are d (i.e. dextro-rotary) -limonene, $\alpha$-terpinene, p-menthene and carvomenthene; within this class can also be included monocyclic ketones, e.g. carvone, $\alpha$- or $\beta$-ionone, which is derived by reacting citral with acetone; additionally, a typical monocyclic alcohol falling within this class would be $\alpha$- or $\beta$- or $\gamma$-terpineol.

Typical examples of useful bicyclic monoterpenoids are bicyclic terpenes such as $\alpha$- or $\beta$-pinene, camphene, 3-carene, bornylene, and tricyclene. Examples of bicyclic ketones are fenchone, camphor and thujone.

In the aqueous hydrogen peroxide solution, an effective stabilizing concentration for the terpenoid compositions generally falls within the range of 0.05 to 5 percent of the weight of the peroxide solution. Preferably, the terpenoid concentration falls within the range of 0.25 to 1.4 weight percent.

Oxidation dye concentrates that are useful in preparing aerosol compositions of this invention are quite varied and well known to those skilled in this art. Typical concentrates that may be employed herein are described in Sagarin "Cosmetics, Science and Technology", Interscience Publishers, Inc., New York (1957) at pages 503–512 this being incorporated herein by way of reference. Other such typical oxidation dye concentrates are described in articles by Gus S. Kass in American Perfumer, July 1956, pages 27–28 (Technology of Modern Oxidation Hair Dyes, Part I) and American Perfumer, September, 1956, pages 48–49 (Technology of Modern Oxidation Hair Dyes, Part III) also incorporated herein by way of reference.

The oxidation dye concentrates used in the present invention comprises essentially a vehicle base or solvent for the oxidation dye intermediates. In more sophisticated preparations it may also contain direct dyes as shade modifiers, antioxidants, stabilizers, sequestering agents, alkalies, etc.

Table I below gives a generalized formulation for oxidation dye concentrates that may be employed in the present invention.

TABLE I

| Ingredients | Oxidation Dye Concentrates | | | |
|---|---|---|---|---|
| | | General | | Preferred |
| Oxidation dye intermediate | | 0.1 to 10 | | .2 to 5 |
| Antioxidant | | 0 to 1 | | 0.2 to 0.5 |
| Alkali | to pH | 8 to 11 | to pH | 9 to 10.5 |
| Vehicle base or solvent | q.s. | to 100% | q.s. | to 100% |

Oxidation dye intermediates, often also referred to as oxidation dyes which are useful in the present invention are illustrated in Table III, page 504 of Sagarin's book mentioned above. Illustrative of these oxidation dyes there can be mentioned the aminodiphenylamines, phenylenediamines, aminophenols, phenols including polyhydric phenols, aminophenol ethers, and their acid addition salts. Such intermediates also often have lower aliphatic substituents on the aryl nucleus or the amino group.

The aminodiphenylamines may have an amino group in one or both of the unsubstituted para positions of the phenyl radicals. Also, the aminodiphenylamines can be sulfonated. Illustrative of aminodiphenylamine oxidation dye intermediates there can be mentioned; p-aminodiphenylamine hydrochloride, p-aminodiphenylamine sulfonic acid; p,p'-diaminodiphenylamine; and the like.

The phenylenediamines useful herein are diaminobenzenes which often also have aliphatic, e.g. lower alkyl radicals on the aromatic ring or on the amino groups. Illustrative of phenylenediamines there can be mentioned: o-phenylenediamine; m-phenylenediamine; p-phenylenediamine; p-phenylenediamine hydrochloride; p-phenylenediamine sulfate; N-(p-aminophenyl) glycine; m-toluenediamine; p-toluenediamine; and the like. Illustrative of other substituted phenylenediamines and derivatives thereof are N,N-dihydroxyethyl-p-phenylenediamine; 4-nitro-o-phenylenediamine; and 2-nitro-p-phenylenediamine.

The aminophenols used here are also often substituted by an additional amino group or sulfo group on the aromatic nucleus or by an alkyl or carboxyalkyl group on the nitrogen. Illustrative of aminophenols there can be mentioned: o-aminophenol; p-aminophenol; p-aminophenol hydrochloride; p-aminophenol sulfate; 2-aminophenol-4-sulfonic acid; 4-aminophenol-2-sulfonic acid; p-methylaminophenol sulfate; 2,4-diaminophenol; 2,4-diaminophenol hydrochloride; 2,5-diaminophenol-4-sulfonic acid; N-(p-hydroxyphenyl) glycine; and the like.

Among phenols employable herein, including polyhydric phenols, mention may be made of pyrocatechol, resorcinol, pyrogallol, α- or β-naphthols, and 1,5-dihydroxynaphthalene; aminophenol ethers include 2,4-diaminoanisole and 2,4-diaminophenetole.

Certain direct dyes may be incorporated in oxidation dye concentrates of the present invention in order to modify the shade. These are most commonly nitro dyes, such as 4-nitro-o-phenylenediamine, 2-nitro-p-phenylenediamine, 4-nitro-2-aminophenol, 2-nitro-4-aminophenol and picramic acid.

To illustrate some of the antioxidants that may be employed in the oxidation dye concentrates used herein mention can be made of sodium sulfite, thioglycolic acid, thioglycerol, sodium hydrosulfite and ascorbic acid.

With respect to the alkalies that may be employed in the oxidation dye concentrates described herein, mention may be made of ammonium hydroxide, monoethanolamine, an alkaline earth hydroxide, alkali metal hydroxides, such as sodium hydroxide, or potassium hydroxide, or carbonates, such as sodium carbonate and bicarbonate.

The "Vehicle base" or solvent mentioned in Table I above is principally water. However, it will also usually contain other adjuvants such as thickening agents, surfactants, other solvents (e.g. propylene glycol, ethanol, isopropanol, etc.).

Any of a variety of surface active agents may be employed in preparing the oxidation dye concentrates employed herein. These can be anionic or non-ionic. Illustrative of the various types of water-soluble or water-dispersible surface active agents there can be mentioned: higher alkylbenzenesulfonates; alkylnaphthalenesulfonates; sulfonated esters of alcohols and polybasic acids; taurates; fatty alcohol sulfates; sulfates of branched chain or secondary alcohols; fatty acid salts; ethoxylated alkyl phenols; and the like. Illustrative of specific surfactants there can be mentioned; sodium lauryl sulfate; polyoxyethlene lauryl ester; glyceryl monostearate; sodium salt of palmitic methyl taurine; lauric diethanolamide; polyoxyethylene stearate; dodecyl benzene sodium sulfonate; nonyl naphthalene sodium sulfonate; dioctyl sodium sulfosuccinate; sodium N-methyl-N-oleoyl taurate; oleic acid ester of sodium isothionate; sodium dodecyl sulfate; the sodium salt of 3,9-diethyl-tridecanol-6-sulfate; ammonium oleate and the like. The quantity of water-soluble surface active agent can vary over a wide range, such as that of from about 0.25% to 15% and preferably from about 0.25% to 10% by weight of the composition.

A thickening agent can also be incorporated in the present oxidation dye concentrates which may be one or several of those commonly used in hair dyeing such as, hydroxyethyl cellulose (DS 0.9 to 1.0 viscosity 53–103 CPS at 25°C); sodium carboxymethyl cellulose (DS 0.65 to 0.85 viscosity 2% aq. sol. 500 CPS at 25°C); commercial methylcellulose (methoxy content 27–31.5% and viscosity 2% aq. sol. at 25°C of 4000 CPS); hydroxybutyl cellulose (Methocel HB), gum arabic, sodium alginate, acrylic polymers such as polyacrylic acid sodium salt, fumed silica, colloidal magnesium aluminum silicate. The thickening agent, when employed will ordinarily constitute between 0.01% to 20% by weight and preferably from about 0.5 to 5% of the total composition.

Any of a number of cosolvents may be used in the oxidation dye concentrate employed in this invention to help solubilize the dyes in the aqueous medium. Typical solvents that are useful for this purpose include ethanol, isopropanol, propylene glycol, ethylene glycol and glycerine.

In preparing the aerosol oxidation dye compositions of this invention, the oxidation dye concentrates described above (97% to 90% by weight) are mixed with the propellant blend of this invention (3 to 10% by weight). In a preferred form of this aspect of the invention, the propellant blend comprises 5% by weight of the total aerosol composition, the balance being made up of concentrate.

In connection with the application of this invention to an oxidation dye dyeing system, use can be made of a double cavity aerosol container in which the oxidation dye composition, hereinafter referred to as the oxidation dye concentrate, and oxidizing agent are maintained in separate compartments within the aerosol container. One such system which is utilizable in accordance with the present invention is described in the U.S. Pat. No. 2,973,883 to Modderno. In this instance, the oxidation dye concentrate together with the propellant blend of the present invention, is placed in the outer compartment of the aerosol can. The oxidizing agent, on the other hand, is contained within the inner flexible tube of the Modderno device. (See tube 28 of FIG. 2 of the Modderno U.S. Pat. No. 2,973,883).

The oxidizing agents are well known in this art for developing the color of the oxidation dye intermediates contained in the oxidation dye concentrate. This will usually take the form of an aqueous composition or solution containing 10 to 20% hydrogen peroxide. Other oxidizing agents may be used in place of the hydrogen peroxide such as urea peroxide; alkali metal chlorates, persulphates, perborates or mixtures thereof, sodium dichromate. However, the oxidizing agent of choice for the present purposes comprises an aqueous solution of hydrogen peroxide.

In employing compositions of the present invention for dyeing hair using an oxidation dye dyeing system in procedure for use is an follows: shake can well to obtain maximum emulsification or solution of propellant. Hold can so that applicator nozzle is close to the hair. Apply foam and work thoroughly through hair. Allow color to develop on the hair and then wash excess color solution off the hair.

Use may be made of any conventional liquified gaseous propellant system together with the hair coloring compositions disclosed herein. Among the most useful and readily available propellants are hydrocarbons such as n-butane, isobutane, halogenated hydrocarbons such as those found under the trade name Freon (e.g. dichlorofluoromethane, trichlorotrifluoromethane, monochlorotrifluoromethane, etc.). Other gas propulsion agents can also be used together with the above propellants. A particularly effective propellant system is one comprising a mixture of 35 weight percent Freon 12 ($CCl_2F_2$); 30 weight percent Freon 152a (1,1-difluoroethane); and 35 weight percent of Freon 114 ($CClF_2$—$CClF_2$).

The following examples are herein given and meant to be merely illustrative of the invention, the scope of which is defined by the appended claims.

In the examples as follows and throughout the disclosure herein, the following terms shall be defined as given below:

1. Ionone AB is a mixture containing 60 ± 10 weight percent of α-ionone and 40 ± 10 weight percent of β-ionone.
2. Tween 20 is an oil-water emulsifier and solubilizer classified as a non-ionic surfactant corresponding chemically to polyoxyethylene (20) sorbitan monolaurate.
3. Brij 35 is an oil-water emulsifier and solubilizer classified as a non-ionic surfactant corresponding chemically to a polyethylene lauryl ether (in which lauryl alcohol has been ethoxylated with 23 moles of ethylene oxide).

EXAMPLE I

Example I is meant to illustrate the effectiveness of typical terpenoid compounds in reducing the pressure within a closed space resulting from the evolution of oxygen by an aqueous hydrogen peroxide solution.

Studies were made of hydrogen peroxide systems in which the conditions were made more rigorous than normally encountered in co-dispensing aerosol hair coloring system containers.

Accordingly, manometric studies were made comparing the oxygen pressure readings after 6 hours at 50°C on the following solutions contained within a closed system:

| Solution A Ingredients | Weight Percent |
|---|---|
| Hydrogen Peroxide | 12.0 |
| Sodium Stannate | 0.02 |
| Deionized water | q.s. to 100 |
| Phosphoric acid | added to yield a pH of 2.5-4 in the final solution |
| Acetic acid (buffer) | 0.4 |
| Solution B | |
| Has the same composition as Solution A but is additionally doped to provide a copper ion concentration of 0.04 parts per million. | |

Additionally, Solutions C to H contain the same ingredients as Solution B with the exception that each solution additionally contained a sufficient amount of a terpenoid compound to give a terpenoid concentration of 0.05 molar and in each solution 2 weight percent (based on the final solution weight) of Tween 20 solubilizer for the terpenoid compounds. The resulting Solutions C through H contained respectively 5 molar percent concentration of the following terpenoids; d-limonene, myrcene, α-pinene, α-terpineol, ionone AB and carvone. The resulting manometer readings after 6 hours at 50°C were as follows:

| Solutions | Pressure, Centimeters Water at Room Temp. |
|---|---|
| A | 20 |
| B | 200 |
| C | 0 |
| D | 0 |
| E | 0 |
| F | 26 |
| G | 24 |
| H | 0 |

EXAMPLE II

In order to illustrate the effectiveness of the terpenoid, d-limonene, in absorbing the excess oxygen which is given off by hydrogen peroxide solutions, the oxygen uptake was measured in oxygen-charged aqueous solutions containing d-limonene and a solubilizer. The drop in oxygen pressure was noted with time for the following samples with and without the terpenoid stabilizer:

| Solution | Oxygen Pressure (Atmospheres) Days | | | | | |
|---|---|---|---|---|---|---|
| | 0 | 5.0 | 20 | 60 | 120 | 180 |
| (A) Water & Oxygen | 5 | 5.0 | 5.0 | 5.0 | 5.0 | 5.0 |
| (B) Sol. A containing concentrations of 0.1 molar d-limonene and 0.7 molar Tween 20 | 5 | 4.7 | 4.2 | 2.8 | 1.7 | 1.4 |
| (C) Sol. A containing a concentration of 0.07 molar Tween 20 | 5 | 4.8 | 4.8 | 4.7 | 4.5 | 4.0 |

Please note that for Examples III – X, a tabular result having the entry * will mean that no determination has been made for that particular dye intermediate.

EXAMPLE III

An oxidation dye concentrate was prepared as an oil-in-water emulsion in which the dye is contained in the oil phase and having the following ingredients:

| INGREDIENT | | WEIGHT PERCENT |
|---|---|---|
| p-phenylenediamine | (hereinafter referred to as dye intermediate "A") | 0.13 |
| N,N-dihydroxy-ethyl-p-phenylenediamine | (hereinafter referred to as dye intermediate "B") | 0.02 |
| Resorcinol | (hereinafter referred to as dye intermediate "C") | 0.09 |
| 4-nitro-o-phenylene-diamine | (hereinafter referred to as dye intermediate "D") | 0.04 |
| 2-nitro-p-phenylene-diamine | (hereinafter referred to as dye intermediate "E") | 0.02 |
| 2,4-diaminoanisole | (hereinafter referred to as dye intermediate "F") | 0.05 |
| p-aminophenol | (hereinafter referred to as dye intermediate "G") | 0.10 |
| Sodium Sulfite | (antioxidant) | 0.1 |
| Ascorbic Acid | (antioxidant) | 0.1 |
| Ethylenediamine-tetraacetic acid | (chelating agent) | 0.05 |
| Ethanol | (solvent) | 10.00 |
| Monoethanolamine | (alkali, Vehicle base) | 9.50 |
| Oleic Acid | (Vehicle base) | 15.00 |
| Sodium lauryl sulfate | (surfactant) | 2.00 |
| Ethyl carbitol | (solvent) | 5.00 |
| Propylene glycol | (Solvent) | 5.00 |
| Octyl-phenoxy-ethyleneoxyethanol | (contains 1 mole ethylene oxide; sold under the trade name Triton X15; non-ionic foaming agent) | 6.00 |
| Nonyl-phenoxy-polyethyleneoxyethanol | (contains 4–5 moles ethylene oxide; non-ionic foaming agent) | 3.00 |
| perfume | | 0.50 |
| water | | 43.30 |
| | | 100.00 |

A propellant mixture was prepared having the following composition:

| Freon 12 | 35 weight percent |
|---|---|
| Freon 152a | 30 weight percent |
| Freon 114 | 35 weight percent |

An aqueous hydrogen peroxide solution was prepared containing 13 weight percent of hydrogen peroxide and sufficient stannate phosphoric acid for a pH of 2.45. The grade of hydrogen peroxide used was that sold by DuPont under the trade name Albone CG which already contains the sodium stannate and phosphoric acid for stabilization purposes.

The above dye concentrate solution, propellant blend, and hydrogen peroxide solution were placed in an aerosol can of the type shown in FIG. 2 of U.S. Pat. No. 2,973,883. The final shade obtainable with this aerosol colorant composition is light brown. Within the inner bag thereof was placed 22 parts by weight of the above peroxide solution. In the interior portion of the aerosol can, which is exterior to the bag containing the hydrogen peroxide solution, was placed 68 parts by weight of the dye concentrate solution and, additionally, 6 parts by weight of the propellant blend.

An aerosol can used for the co-dispensing of hair colorants containing the above ingredients was stored for 4 months at room temperature (i.e. 25°C) and then was compared and analyzed by thin-layer chromatography with a control aerosol can having the exact same ingredients freshly made. The percent of the original dye intermediates remaining in the four-month old can was as follows:

| Dye A | 80 |
|---|---|

-continued

| Dye B | 90 |
|---|---|
| Dye C | 70 |
| Dye D | 90 |
| Dye E | 40 |
| Dye F | * |
| Dye G | 90 |

EXAMPLE IV

The procedure of Example III was repeated except that the hydrogen peroxide solution additionally contained 0.4 weight percent of a terpenoid mixture containing 70 parts by weight of d-limonene and 30 parts by weight of α-terpineol, and Tween 20 solubilizer. The pH was 2.45. The resulting analysis for the percentage of original dye intermediates remaining in the aerosol can is as follows:

| Dye A | 100 |
|---|---|
| Dye B | 100 |
| Dye C | 80 |
| Dye D | 100 |
| Dye E | 60 |
| Dye F | * |
| Dye G | 100 |

EXAMPLE V

The procedure of Example III was repeated except that the temperature of storage was 38°C. The resulting analysis for the percentage of original dye intermediates remaining in the aerosol can is as follows:

| Dye A | 70 |
|---|---|
| Dye B | 90 |
| Dye C | 60 |

-continued

| | |
|---|---|
| Dye D | 80 |
| Dye E | 30 |
| Dye F | * |
| Dye G | 90 |

EXAMPLE VI

The procedure of Example IV was repeated except that the temperature of storage was 38°C. The resulting analysis for the percentage of original dye intermediates remaining in the aerosol can is as follows:

| | |
|---|---|
| Dye A | 100 |
| Dye B | 100 |
| Dye C | 70 |
| Dye D | 90 |
| Dye E | 40 |
| Dye F | * |
| Dye G | 100 |

EXAMPLE VII

The procedure of Example III was repeated except that the pH was 3.65. The resulting analysis for the percentage of original dye intermediates remaining in the aerosol can is an follows:

| | |
|---|---|
| Dye A | 90 |
| Dye B | * |
| Dye C | 50 |
| Dye D | 90 |
| Dye E | * |
| Dye F | 80 |
| Dye G | 80 |

EXAMPLE VIII

The procedure of Example VII was repeated except that the hydrogen peroxide solution additionally contained 0.4 weight percent of a terpenoid mixture containing 70 parts by weight of d-limonene and 30 parts by weight of α-terpineol, and Brij 35 solubilizer. The pH was 3.60. The resulting analysis for the percentage of original dye intermediates remaining in the aerosol can is as follows:

| | |
|---|---|
| Dye A | 100 |
| Dye B | * |
| Dye C | 100 |
| Dye D | 100 |
| Dye E | * |
| Dye F | 100 |
| Dye G | 100 |

EXAMPLE IX

The procedure of Example VII was repeated except that the storage temperature is 38°C. The resulting analysis for the percentage of original dye intermediates remaining in the aerosol can is as follows:

| | |
|---|---|
| Dye A | 80 |
| Dye B | * |
| Dye C | 40 |
| Dye D | 90 |
| Dye E | * |
| Dye F | 70 |
| Dye G | 80 |

EXAMPLE X

The procedure of Example VIII was repeated except that the storage temperature is 38°C. The resulting analysis for the percentage of original dye intermediates remaining in the aerosol can is as follows:

| | |
|---|---|
| Dye A | 100 |
| Dye B | * |
| Dye C | 60 |
| Dye D | 100 |
| Dye E | * |
| Dye F | 100 |
| Dye G | 100 |

EXAMPLE XI

A further illustration of the effectiveness of the terpenoid compounds in controlling the amount of oxygen released by hydrogen peroxide solutions is given by comparing the percentage increase in the volume of an aluminum-laminated bag containing an aqueous hydrogen peroxide solution with and without the terpenoid stabilizers. Accordingly, three flexible bags of the type used in aerosol co-dispensing cans having the same size were utilized. An aqueous hydrogen peroxide solution having the same composition as that given for Solution A in Example I was placed in the first bag. In the second bag was placed a similar solution to that in the first bag but additionally containing 1.4 weight percent of d-limonene and a sufficient amount of Tween 20 solubilizer. In the third bag was placed a similar solution to that contained in the first bag but additionally containing 0.3 weight percent of d-limonene, and 0.1 weight percent of α-terpineol and a sufficient amount of Tween 20 solubilizer. The three bags were then stored for 1 month at a temperature of 50°C. The percentage increase in the bag volume based on the original size, which can be attributed to the oxygen content contained in the bag, was as follows:

| SAMPLE | | PERCENTAGE INCREASE IN ORIGINAL BAG VOLUME |
|---|---|---|
| BAG 1 | contains no monoterpenoids | +53 |
| BAG 2 | contains 1.4 percent d-limonene | +13 |
| BAG 3 | contains 0.3 percent d-limonene +0.1 percent α-terpineol | +21 |

What is claimed is:
1. An aerosol oxidation hair dyeing composition in an aerosol container under pressure wherein prior to re- lease the composition is physically separated into mixtures A and B wherein:
  a. mixture A comprises a stabilized aqueous hydrogen peroxide solution comprising from about 10 to 20 weight percent of hydrogen peroxide, from about 0.25 to 1.4 weight percent of at least one monoterpenoid compound wherein the chemical structure of said compound is acyclic, monocyclic or bicyclic, and water wherein the pH of mixture A is about 2.5 to 4; and
  b. mixture B is an aerosol hair dye composition comprising a propellant blend and an aqueous oxidation hair dye concentrate, said concentrate containing at least one oxidation dye intermediate whose color is developable by means of an oxidizing agent, wherein the pH of mixture B is about 8 to 11.

2. The composition of claim 1 wherein said concentrate comprises about 90 to 97 weight per cent of mixture B and said propellant blend comprises about 3 to 10 weight per cent of mixture B.

3. The composition of claim 1 wherein said monoterpenoid compound is selected from the group consisting of d-limonene, myrcene, pinene, terpineol, ionone and carvone.

4. The composition of claim 3 wherein said monoterpenoid compound is d-limonene.

* * * * *